US008696601B2

(12) United States Patent
Deacon et al.

(10) Patent No.: US 8,696,601 B2
(45) Date of Patent: *Apr. 15, 2014

(54) SYSTEMS AND METHODS FOR OCULAR MEASUREMENTS

(75) Inventors: Jim Deacon, Goleta, CA (US); Edward Geraghty, Rancho Santa Margarita, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/561,849

(22) Filed: Jul. 30, 2012

(65) Prior Publication Data
US 2013/0274627 A1    Oct. 17, 2013

Related U.S. Application Data

(63) Continuation of application No. 13/214,972, filed on Aug. 22, 2011, now Pat. No. 8,231,672, which is a continuation of application No. 12/412,338, filed on Mar. 26, 2009, now Pat. No. 8,002,827, which is a continuation-in-part of application No. 11/739,392, filed on Apr. 24, 2007, now Pat. No. 7,993,398.

(60) Provisional application No. 61/040,638, filed on Mar. 28, 2008.

(51) Int. Cl.
| A61B 5/103 | (2006.01) |
| A61B 5/117 | (2006.01) |
| A61F 2/14  | (2006.01) |
| A61F 2/16  | (2006.01) |

(52) U.S. Cl.
USPC ........... 600/587; 623/4.1; 623/5.11; 623/5.12

(58) Field of Classification Search
USPC ............... 600/587; 623/4.1, 5.11, 5.12, 6.11, 623/6.38, 6.39, 6.43, 6.44, 6.47, 6.51
See application file for complete search history.

(56) References Cited

U.S. PATENT DOCUMENTS

| 4,077,071 A | 3/1978 | Freeman |
| 4,093,361 A | 6/1978 | Erickson et al. |

(Continued)

FOREIGN PATENT DOCUMENTS

| DE | 8107675 U1 | 7/1981 |
| EP | 957331 A2 | 11/1999 |

(Continued)

OTHER PUBLICATIONS

Alio J.L., et al., "Phakic anterior chamber lenses for the correction of myopia: a 7-year cumulative analysis of complications in 263 cases," Ophthalmology, 1999, vol. 106 (3), pp. 458-466.

(Continued)

*Primary Examiner* — Max Hindenburg
*Assistant Examiner* — Adam Eiseman
(74) *Attorney, Agent, or Firm* — Abbott Medical Optics Inc.

(57) ABSTRACT

A system for measuring the size of a capsular bag of an eye of a subject includes a size indicator and a sizing gauge. The size indicator is configured for insertion into a capsular bag and includes a peripheral portion and a pair of arms. The peripheral portion is configured to engage the capsular bag. Each of the arms has a proximal end and a distal end, the arms being joined to one another at the proximal ends. The peripheral portion is joined to the distal ends of the arms. The arms form an angle that depends on a size of the capsular bag into which the size indicator is placed.

5 Claims, 8 Drawing Sheets

(56) References Cited

U.S. PATENT DOCUMENTS

| | | | |
|---|---|---|---|
| 4,134,160 A | 1/1979 | Bayers | |
| 4,174,543 A | 11/1979 | Kelman | |
| 4,249,272 A | 2/1981 | Poler | |
| 4,254,509 A | 3/1981 | Tennant | |
| 4,254,510 A | 3/1981 | Tennant | |
| 4,316,293 A | 2/1982 | Bayers | |
| 4,319,564 A | 3/1982 | Karickhoff | |
| 4,370,760 A | 2/1983 | Kelman | |
| 4,377,873 A | 3/1983 | Reichert, Jr. | |
| 4,403,353 A | 9/1983 | Tennant | |
| 4,404,694 A | 9/1983 | Kelman | |
| 4,424,597 A | 1/1984 | Schlegel | |
| 4,446,581 A | 5/1984 | Blake | |
| 4,480,340 A | 11/1984 | Shepard | |
| 4,551,864 A | 11/1985 | Akhavi | |
| 4,556,998 A | 12/1985 | Siepser | |
| 4,560,383 A | 12/1985 | Leiske | |
| 4,605,409 A | 8/1986 | Kelman | |
| 4,605,411 A | 8/1986 | Fedorov et al. | |
| 4,629,460 A | 12/1986 | Dyer | |
| 4,629,462 A | 12/1986 | Feaster | |
| 4,676,791 A | 6/1987 | LeMaster et al. | |
| 4,676,792 A | 6/1987 | Praeger | |
| 4,681,102 A | 7/1987 | Bartell | |
| 4,687,484 A | 8/1987 | Kaplan | |
| 4,687,485 A | 8/1987 | Lim et al. | |
| RE32,525 E | 10/1987 | Pannu | |
| 4,725,277 A | 2/1988 | Bissonette | |
| 4,734,095 A | 3/1988 | Siepser | |
| 4,781,717 A | 11/1988 | Grendahl | |
| 4,787,904 A | 11/1988 | Severin et al. | |
| 4,834,748 A | 5/1989 | McDonald | |
| 4,863,539 A | 9/1989 | Lee et al. | |
| 4,997,442 A | 3/1991 | Barrett | |
| 5,019,097 A | 5/1991 | Knight et al. | |
| 5,047,052 A | 9/1991 | Dubroff | |
| 5,071,432 A | 12/1991 | Baikoff | |
| 5,078,742 A | 1/1992 | Dahan | |
| 5,133,749 A | 7/1992 | Nordan | |
| 5,147,395 A | 9/1992 | Willis | |
| 5,147,397 A | 9/1992 | Christ et al. | |
| 5,184,405 A * | 2/1993 | Cress | 33/1 SD |
| 5,197,981 A | 3/1993 | Southard | |
| 5,201,763 A | 4/1993 | Brady et al. | |
| 5,203,790 A | 4/1993 | McDonald | |
| 5,217,491 A | 6/1993 | Vanderbilt | |
| 5,225,858 A | 7/1993 | Portney | |
| 5,258,025 A | 11/1993 | Fedorov et al. | |
| 5,433,745 A | 7/1995 | Graham et al. | |
| 5,476,513 A | 12/1995 | Brady et al. | |
| 5,628,796 A | 5/1997 | Suzuki | |
| 5,691,800 A | 11/1997 | Iki et al. | |
| 5,716,403 A | 2/1998 | Tran et al. | |
| 5,801,807 A | 9/1998 | Satake et al. | |
| 5,928,282 A | 7/1999 | Nigam | |
| 6,015,435 A | 1/2000 | Valunin et al. | |
| 6,051,024 A | 4/2000 | Cumming | |
| 6,129,759 A | 10/2000 | Chambers | |
| 6,179,870 B1 | 1/2001 | Sourdille et al. | |
| 6,235,055 B1 | 5/2001 | Chu | |
| 6,261,321 B1 | 7/2001 | Kellan | |
| 6,319,282 B1 | 11/2001 | Nishi | |
| 6,419,697 B1 | 7/2002 | Kelman | |
| 6,598,606 B2 | 7/2003 | Terwee et al. | |
| 7,455,407 B2 | 11/2008 | Neal et al. | |
| 7,616,330 B2 | 11/2009 | Neal et al. | |
| 7,794,497 B2 | 9/2010 | Brady et al. | |
| 2001/0051825 A1 | 12/2001 | Peterson | |
| 2002/0173846 A1 | 11/2002 | Blake et al. | |
| 2004/0054358 A1 | 3/2004 | Cox et al. | |
| 2004/0068317 A1 | 4/2004 | Knight | |
| 2004/0167622 A1 | 8/2004 | Sunalp et al. | |
| 2005/0251254 A1 | 11/2005 | Brady et al. | |
| 2006/0020268 A1 | 1/2006 | Brady et al. | |
| 2006/0068453 A1 | 3/2006 | Altieri | |
| 2007/0268453 A1 | 11/2007 | Hong et al. | |
| 2008/0018910 A1 | 1/2008 | Neal et al. | |
| 2008/0231809 A1 | 9/2008 | Haigis | |
| 2008/0269642 A1 | 10/2008 | Deacon et al. | |

FOREIGN PATENT DOCUMENTS

| | | |
|---|---|---|
| FR | 2745711 A1 | 9/1997 |
| WO | WO9856315 A1 | 12/1998 |
| WO | WO0135868 A1 | 5/2001 |
| WO | WO0154569 A1 | 8/2001 |
| WO | WO2006032263 A2 | 3/2006 |

OTHER PUBLICATIONS

Apple D.J., et al., "Anterior Chamber Lenses Part 1: Complications and Pathology and a Review of Designs," Journal of Cataract Refractive Surgery, 1987, vol. 13 (2), pp. 157-174.

Apple D.J., et al., "Intraocular Lens Evolution, Designs," Complications and Pathology, 1989, vol. 22 (36), pp. 205-221.

Apple D.J., et al., "Intraocular Lenses: Evolution, Designs, Complications and Pathology," 1989, vol. 36 (1), pp. 22-36.

Baikoff G., et al., "Angle-fixated Anterior Chamber Phakic Intraocular Lens for Myopia 7 to -19 Diopters," Journal of Refractive Surgery, 1998, vol. 14 (3), pp. 282-292.

CILCO Advertisement Brochure, Oct. 1982, 3 pages.

International Preliminary Report on Patentability for Application No. PCT/US08/061180, mailed on Oct. 27, 2009, 1 page.

International Preliminary Report on Patentability for Application No. PCT/US2009/038469, mailed on Sep. 28, 2010, 1 page.

International Search Report and Written opinion for Application No. PCT/US08/061180, mailed on Sep. 5, 2008, 10 pages.

International Search Report and Written opinion for Application No. PCT/US09/038469, mailed on Aug. 10, 2009, 12 pages.

Kim J.H., et al., "The Analysis of Predicted Capsular Bag Diameter using Modified Model of Capsule Measuring Ring in Asians," Clinical and Experimental Ophthalmology, 2008, vol. 36 (3), pp. 238-244.

Marinho, "Results are encouraging for phakic IOLs, but more work is needed," Ocular Surgery News, Refractive Surgery, pp. 12-15, 2000.

Menapace R., et al., "Capsular Tension Rings," Cataract and Refractive Surgery, 2008, pp. 27-44.

Praeger D.L., Copeland Lens, 1982, 7 pages.

Strenn K., et al., "Capsular bag Shrinkage after Implantation of an Open-loop silicone lens and a Poly(methyl methacrylate) Capsule Tension Ring," Journal of Cataract and Refractive Surgery, 1997, vol. 23 (10), pp. 1543-1547.

Tehrani M., et al., "Capsule Measuring Ring to Predict Capsular Bag Diameter and Follow its Course after Foldable Intraocular Lens Implantation," Journal of Cataract Refractive Surgery, 2003, vol. 29 (11), pp. 2127-2134.

U.S. Appl. No. 11/739,392, filed Apr. 24, 2007.

Vass C., et al., "Prediction of Pseudophakic Capsular bag Diameter based on Biometric Variables," Journal of Cataract and Refractive Surgery, 1999, vol. 25 (10), pp. 1376-1381.

WO 01/54569 Machine Translation. Manfred Tetz and Stephan Schruender. May 12, 2000.

* cited by examiner

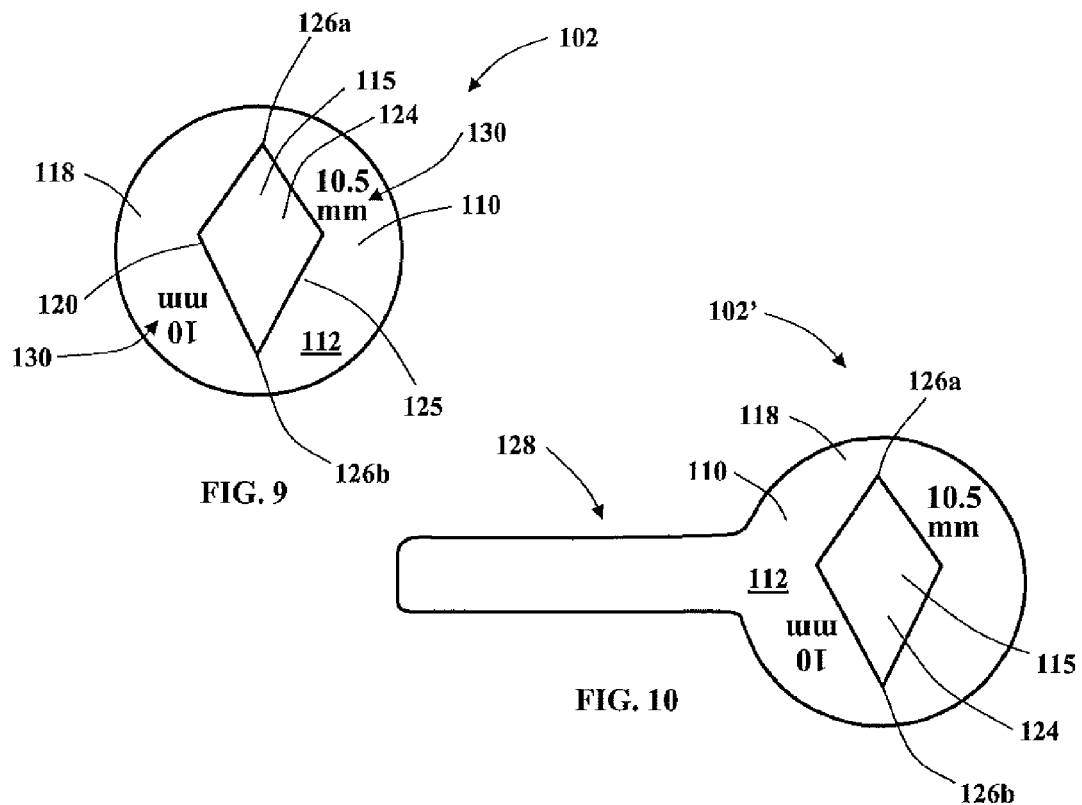
FIG. 9
FIG. 10
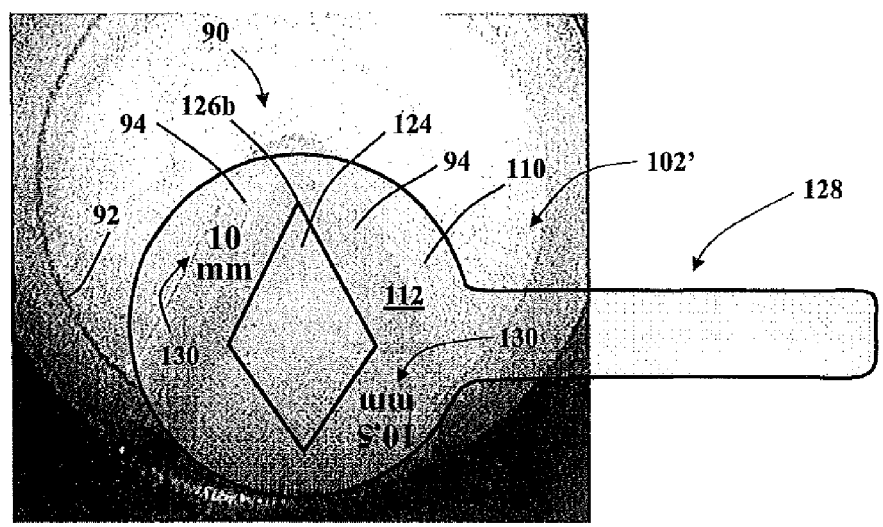
FIG. 11

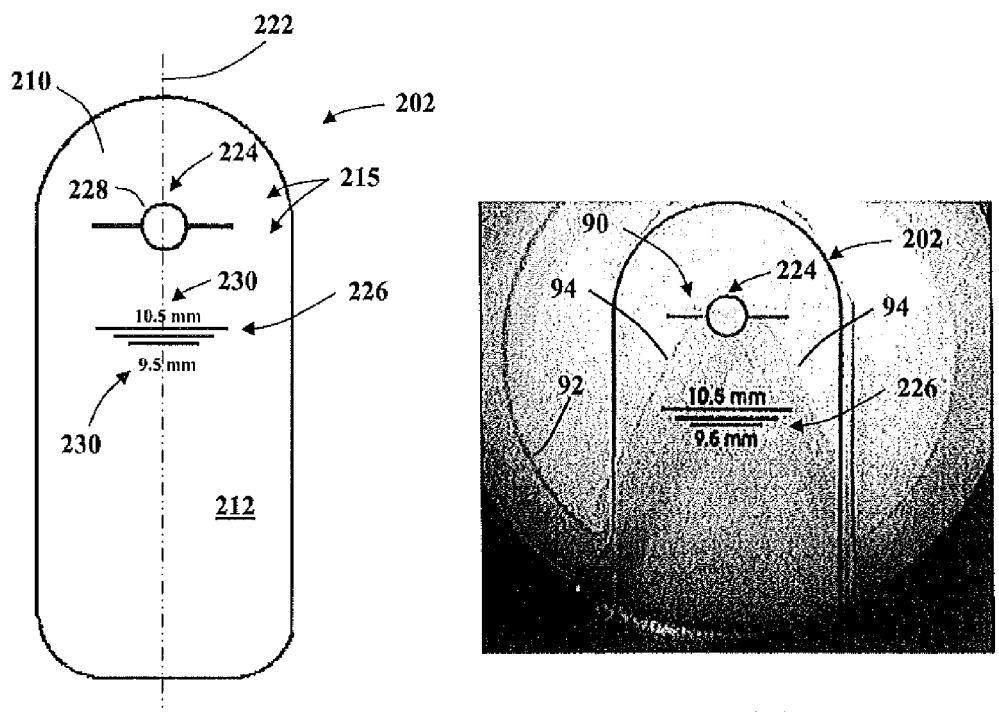
FIG. 12
FIG. 13
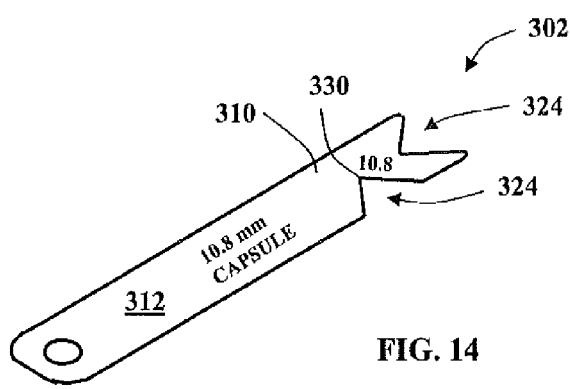
FIG. 14

SYSTEMS AND METHODS FOR OCULAR MEASUREMENTS

RELATED APPLICATION

The present application claims priority under 35 U.S.C §119(e) to provisional application No. 61/040,638, filed on Mar. 28, 2008 and to U.S. patent application Ser. No. 11/739,392, filed Apr. 24, 2007, the entire contents of each of which applications are hereby incorporated by reference in their entirety for all purposes as if fully set forth herein.

BACKGROUND OF THE INVENTION

1. Field of the Invention

The present invention relates generally to devices, systems, and methods for making and using ocular measurements, more particular for making and using ocular measurements of a cavity size within an eye such as the capsular bag of a human eye.

2. Description of the Related Art

A great deal of effort has been devoted to developing an accommodating intraocular lens, which can adjust its power over a particular range to clearly view both near and far objects. The accommodating intraocular lens is generally inserted into a capsular bag, a transparent structure of an eye that houses the natural lens and generally remains in the eye after the natural lens has been surgically removed.

The accommodating intraocular lens changes its power and/or axial location in response to a squeezing and/or expanding force applied to the lens by the capsular bag via the ciliary muscle.

It is generally important to know the size (or more precisely, the inner diameter or circumference) of the capsular bag for each patient's eye prior to insertion of an intraocular lens. The capsular bag size may vary patient-to-patient or eye-to-eye of the same patient, and if the bag is larger or smaller than expected, the lens may end up slightly expanded or squeezed upon implantation. This, in turn, may result in a shift in the nominal base power and/or a reduction in the accommodation range.

Although the capsular bag diameter is a desirable and useful quantity, it is also quite difficult to measure accurately. There have been various attempts to measure the capsular bag size with ultrasound. While ultrasound may be useful for determining the central thickness of the natural crystalline lens, it is not generally versatile enough to image the entire lens, and cannot reliably read out to the perimeter of the lens.

There have also been attempts to measure the capsular bag by inserting a capsular tension ring (CTR) into the eye. See, for instance, K. STRENN, R. MENAPACE, and C. VASS, "Capsular bag shrinkage after implantation of an open-loop silicone lens and a poly(methyl methacrylate) capsule tension ring," J Cataract Refract Surg, 1997, pp. 1543-1547, Vol. 23, which is hereby incorporated by reference in its entirety. In this reference, a CTR indicates the capsular diameter, based on linear measurement of a peripheral gap. After the measurement, the CTR is generally not removed from the eye and remains resident in the eye, which may be undesirable.

There have been attempts to correlate capsular bag size with other eye properties that can be measured more easily. See, for instance, C. VASS, R. MENAPACE, K. SCHMETTERER, O. FINDL, G. RAINER AND I. STEINECK, "Prediction of pseudophakic capsular bag diameter based on biometric variables," J Cataract Refract Surg, October 1999, pp. 1376-1381, Vol. 25, which is hereby incorporated by reference in its entirety. In this reference, measurements of capsular bag diameter were taken on a sample of patients, using the CTR noted above. In addition, measurements of corneal power and axial length were taken on the same patients, using known methods. A regression analysis of the measurements produced a statistically significant correlation between capsular bag diameter and corneal power and axial length, but not with a sufficient accuracy for predicting the required size of an accommodating intraocular lens.

There have also been attempts to convert the capsular bag circumference dimension to a linear dimension, then to measure the linear dimension with a camera or visually. See, for instance, M. TEHRANI, H. B. DICK, F. KRUMMENAUER, G. PFIRRMANN, T. BOYLE and B. STOFFELNS, "Capsule measuring ring to predict capsular bag diameter and follow its course after foldable intraocular lens implantation," J Cataract Refract Surg, November 2003, pp. 2127-2134, Vol. 29, which is hereby incorporated by reference in its entirety. In this reference, a Koch capsule measuring ring is inserted into the eye. The ring is an incomplete circle, with appendices on each end, so that when the ring is inserted into the capsular bag, the separation between the appendices is related to the capsular bag circumference. The ring is left in the eye after the measurement is taken, which may be undesirable.

In addition, for the above reference, the measurement of the appendix separation may be disadvantageous for two reasons. First, the measurement is taken at the peripheral edge of the eye, which is a difficult region for eye measurements. For instance, the region to be measured might be outside the area of the pupil, and might require the use of a slit lamp, or unusual and undesirable handling of the pupil. Second, it is generally difficult to measure a linear dimension in the eye. Often, such a measurement is taken through the cornea, which can magnify the linear dimension, especially at the periphery of the eye. Because corneal powers may vary from patient-to-patient and eye-to-eye, there may be uncertainty in any linear measurements taken through the cornea. In addition, because most eye surgery is performed through a microscope, the measurement may have to be taken through the microscope, which may have a zoom feature or a variable focal length that may further complicate a linear dimension measurement.

Accordingly, there exists a need for an apparatus and method for measuring the size of the capsular bag of an eye that is relatively simple and accurate, and does not rely on a linear measurement at the periphery of the eye.

BRIEF DESCRIPTION OF THE DRAWINGS

FIG. 9 is a plan view of a sizing gauge according to an embodiment of the present invention.

FIG. 10 is a plan view of a sizing gauge according to an embodiment of the present invention that includes a handle or grip.

FIG. 11 is a plan view of a system according to an embodiment of the present invention where a sizing gauge is disposed over an angle indicator placed within the capsular bag of a subject eye.

FIG. 12 is a plan view of another embodiment of a sizing gauge incorporating a plurality of linear marks or line segments.

FIG. 13 is a plan view of a system according to an embodiment of the present invention where the sizing gauge of FIG. 12 is disposed over an angle indicator placed within the capsular bag of a subject eye.

FIG. 14 is a perspective view of another embodiment of a sizing gauge that comprises two notches or wedge-shaped portions.

DETAILED DESCRIPTION OF THE DRAWINGS

Figure 1:
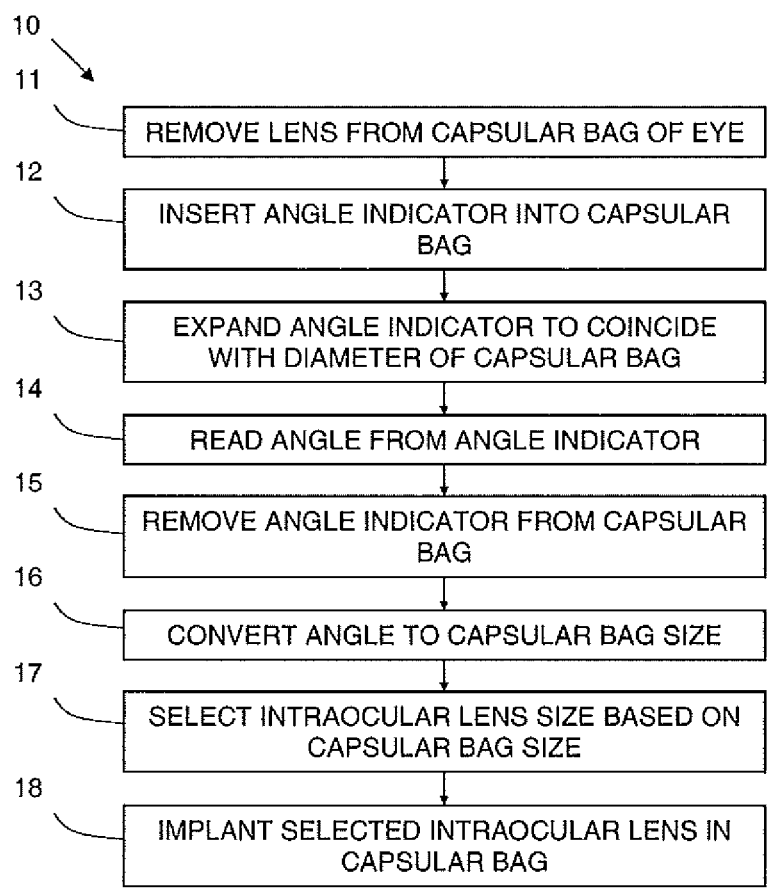
FIG. 1 is a flow chart of a method of replacing a lens in the capsular bag of an eye.

Implantation of an intraocular lens in an eye may require the accurate measurement of the size, position, or other property of the capsular bag of the eye. Embodiments of the present invention are generally directed devices, systems, and methods for determining the size, extent, location, or physical property of a capsular bag or other cavities of a subject eye. While such devices, systems, and methods may be used in conjunction with any intraocular lens or similar device to be placed within a capsular bag, embodiments of the present invention may be particularly useful when used with accommodating intraocular lenses, where function of the intraocular lens may be particularly sensitive to fit of the lens inside the capsular bag.

In some embodiments, the natural crystalline lens is surgically removed and a size indicator is subsequently inserted into the capsular bag for measuring a size or other property of the capsular bag. As used herein, the term "size" means the extent of an object and includes at least the diameter, circumference, cross-sectional area, and volume of an object (e.g., of the capsular bag of an eye). As used herein the term "size indicator" means a physical device that changes size or shape when placed inside the capsular bag of an eye, or some other part of an eye, and is configured to allow an estimate or measurement of a size of the size indicator itself and/or a size, shape, or physical property of the capsular bag or cavity into which the device is placed, the estimate or measurement being based on a visible size or shape of one or more elements of the size indicator. In some cases, the size indicator may be used for determining the position of the capsular bag, for example, relative to the pupil of the eye. When a size of a capsular bag is measured or estimated, the size may be an actual size of a capsular bag at the time of the measurement or a size of the capsular upon or after implantation of an intraocular lens or similar ophthalmic device.

In some embodiments, the size indicator is visually inspected by a user to make an estimate of size of the size indicator and/or the capsular bag or other part of the eye. In such embodiments, a geometric feature of the size indicator may be compared to a feature of a measurement device or to a template showing different configurations of the geometric feature being inspected. In other embodiments, the size indicator is part of a measurement system that also includes a measurement device configured for estimating or measuring a size of one or more elements of the measurement device, either by eye or using a digitized image and analysis software or algorithms.

In certain embodiments, the size indicator is an angle indicator. As used herein the term "angle indicator" is a size indicator in which an angle between two elements or arms of the angle indicator may be observed, estimated, or measured in order to determine a size of the angle indicator itself and/or a size or other property of a capsular bag or other part of an eye into which the angle indicator is placed.

FIG. 1 is a flow chart of an exemplary method 10 for using an angle indicator for replacing a lens in the capsular bag of an eye.

In element 11, a lens is removed from a capsular bag of an eye. The removed lens may be the natural crystalline lens of the eye, which may have become opaque due to cataracts or become damaged by some other disease or injury. Alternatively, the removed lens may be an existing intraocular lens that is being replaced. Typically, the lens is removed in a surgical procedure in which the lens is broken up and vacuumed out of the eye. The capsular bag, which supports the lens before removal, is generally retained for support of the replacement lens.

The replacement lens may be an intraocular lens, such as an accommodating intraocular lens, which relies on forces transferred by the zonular fibers in the eye to the capsular bag and/or on forces produced by a resiliency of the capsular bag itself. These forces can change the power and/or location of the lens by change the lens shape and/or translating one or both of the lens surfaces. The ocular force exerted by the ciliary muscle, capsular bag, and/or zonular fibers is generally limited, and typically the accommodating intraocular lens is designed to use this limited force to change power to cover all or part of a desired range of accommodation for the eye. As a result, the intraocular lens may be quite sensitive to compressive or expansive forces applied to its equator. Importantly, a particular accommodating intraocular lens may be designed to work optimally for a specific capsular bag size or size range. If the patient's capsular bag is larger or smaller than expected, the intraocular lens may experience a shift in nominal power, or a truncation of the accommodation range, which may be undesirable. Accordingly, it may be useful during a surgical procedure to accurately measure the size of the capsular bag, so that an intraocular lens may be selected for implantation that corresponds to the actual size of the capsular bag or provides a predetermined fit within the capsular bag.

In element 12, an angle indicator, is inserted into the capsular bag. During insertion, it is often desirable to use as small an incision as possible, so the angle indicator may optionally be inserted in a folded state.

In element 13, the angle indicator is expanded to coincide with a size or diameter of the capsular bag. If the angle indicator is inserted in a folded state, it may be first unfolded to reach its full size. The capsular bag material is flexible, so that it may be bent and reshaped. It may be relatively straightforward to position the angle indicator, which may be generally ring-shaped, along the equator of the capsular bag. Typically, some gentle, back-and-forth motions applied by the surgeon are sufficient to move the angle indicator to lie along the equator of the capsular bag. In general, the shape of the empty capsular bag is such that it may be well-approximated as circular when viewed from the front. Any azimuthal errors in the positioning of the angle indicator generally do not significantly affect the angular reading from the angle indicator, or the measured value for the capsular bag size.

In element 14, once the angle indicator is aligned along the equator of the capsular bag and the angle is read from the angle indicator. The angle may be formed from the intersection of two generally straight elements on the angle indicator. In some embodiments, the intersection is substantially centrally disposed within the pupil of an eye into which it has been placed, for example, to aid in measuring the angle thus formed. Alternatively, the straight elements of the angle indicator may be relatively long (e.g., to provide a predetermined sensitivity), wherein the intersection between the two generally straight elements may be near the edge of the pupil or outside the pupil. The angle may be seen visually by the surgeon or by a camera or microscope trained on the subject eye. Alternatively or additionally, the angle may be determined by producing an electronic or digital image of the angle indicator and processing the image using software or algorithms to analyze the image.

In element 15, once the angle has been read, the angle indicator may be removed from the capsular bag of the eye. The angle indicator may be folded upon itself for removal, which is especially convenient if the angle indicator is inserted in the folded state. Alternatively, the angle indicator may be broken or separated into segments, and then the segment may be removed through the incision in the eye. In one embodiment, the angle indicator includes cutaways on its posterior surface, or other location, which may allow sectioning in vivo for removal of the angle indicator.

In element 16, the read angle is converted to a capsular bag size or other property of the capsular bag. The size may be reported as a diameter, or, equivalently, as a circumference. The conversion may be done by reading values off a printed table, by reading values off a graph, by plugging the read angle into a predictive formula, by a computer, or directly by comparing the angle to a dedicated device. Alternatively or additionally, the location of the capsular bag may be determined within the eye, for example, relative to the location of the pupil or the macula.

In element 17, once element 16 has produced a value of the capsular bag size, an intraocular lens may be selected or otherwise specified (e.g., the parameters of a custom lens may be specified). The lens selection or specification may be based in part on the capsular bag size, as well as on other data, such as the required lens power, an available amount of accommodative force, and/or a targeted range of accommodation.

For instance, for a given required nominal lens power, there may be several intraocular lenses available, each sized for a particular capsular bag diameter. The available lenses may be part of a kit, with diameter spacings of 0.5 mm, 0.25 mm, 0.2 mm, 0.15 mm, 0.1 mm, 0.05 mm, or any suitable value. Typically, the exact size value given from element 16 may not be exactly available in the kit, and the surgeon or practitioner may have to round off to the nearest size that is available in the kit or specify a custom lens.

Alternatively, the intraocular lens may have an adapter that can be attached to the circumference of the lens, which allows a single lens to be used with multiple sizes of capsular bags.

As a further alternative, the intraocular lens may itself be adjustable, for instance, with an adjustable haptic that can couple a particular optic to a capsular bag sized within a particular range.

In element 18, once an intraocular lens is selected from element 17, the selected lens may be surgically implanted in the capsular bag.

Note that element 15 follows element 14, and elements 16 and 17 follow element 14, but elements 16 and 17 need not follow element 15. For instance, element 15 may follow element 17, which follows element 16, which follows element 14. The conversion of the read angle to a capsular bag size and the selection of a lens based on the capsular bag size are essentially independent of removal of the angle indicator from the capsular bag, and these elements may be performed in any suitable order.

Figure 2:
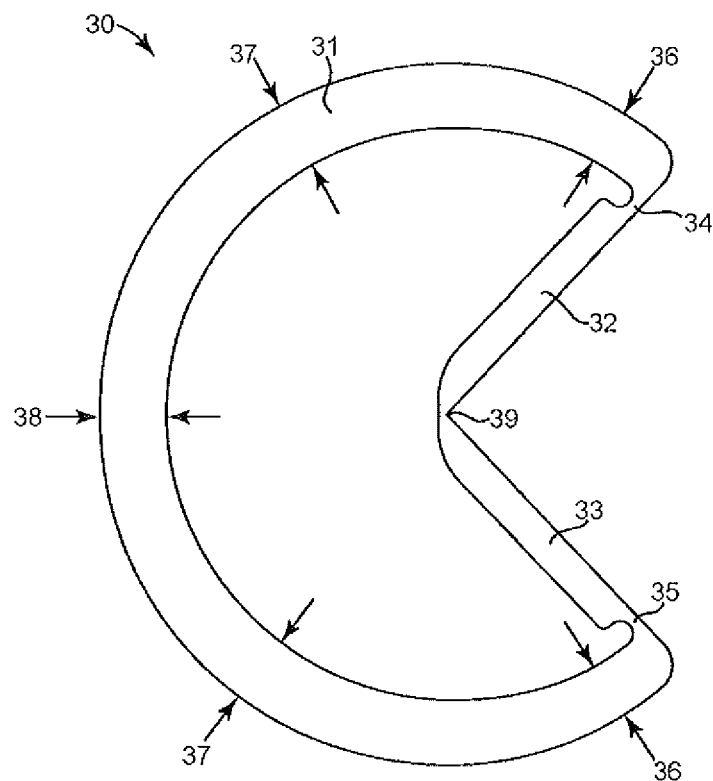
FIG. 2 is a front-view plan drawing of an angle indicator according to an embodiment of the present invention.

Referring to FIG. 2, an angle indicator 30 suitable for use with the method 10 is shown. The angle indicator 30 comprises a broken ring or incomplete annulus 31, with the broken portion of the ring replaced by two arms, segments, or straight sections 32 and 33 that connect to the broken ring 31 and are hingedly connected to each other at a location within the interior of the broken ring 31. The angle indicator is inserted into the capsular bag and the ring 31 expands until it is coincident with a diameter of the capsular bag. As the ring itself expands and contracts, the angle between the two segments increases and decreases. The angle indicator 30 is generally configured to provide an indication or measurement of a capsular bag size or other property independent, or at least substantially independent, of corneal or camera magnifications. The size indicator 30 extends into the center of the capsular bag and is compliant, so that it may be safely removed by grasping the central features and withdrawing it from the capsular bag. Additionally or alternatively, the size indicator 30 may be used for sizing other portions of the eye such as the sulcus or anterior chamber of the eye. The shape or shape change may be measured visually by eye, with or without the use of an external gauge or template, or may be measured using a camera and associated image processing software.

Figure 3:
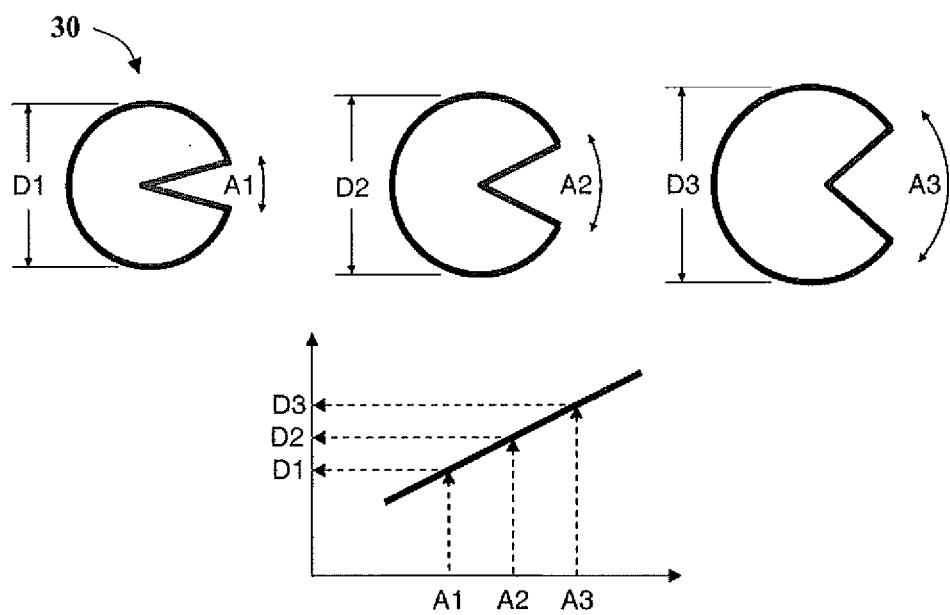
FIG. 3 is a schematic drawing of the angle indicator of FIG. 2 at three exemplary capsular bag sizes.

With additional reference to FIG. 3, the angle indicator 30 is designed so that a relatively small change in diameter of the ring 31 produces a relatively large change in angle between arms 32, 33. For instance, three exemplary diameters D1, D2 and D3, are shown in FIG. 3, along with their corresponding angles A1, A2 and A3. The relationship between measured angle and ring (and, therefore, capsular bag) diameter is shown in the exemplary plot in FIG. 3. Note that the relationship need not be truly linear, as shown in FIG. 3, but may have any suitable increasing relationship, such as a quadratic or more complex polynomial relationship. During use, the practitioner inserts the angle indicator 30 into the capsular bag, expands the angle indicator 30 to fill the capsular bag, reads the angular value from angle indicator 30, and converts the read angular value to a capsular bag diameter, or equivalently, circumference.

Note that the angle is viewable near the center of the pupil of the lens, rather than only at the edge of the pupil or the edge of the capsular bag. This reduces the need for unusual viewing techniques, or extra handling of the pupil, and may help reduce distortion of the angle when viewed through the patient's cornea.

In one embodiment, the angle indicator 30 remains substantially round, for all angles/diameters within a particular range. This is accomplished by varying the radial thickness of the ring, with a maximum thickness opposite the two segments, and a minimum thickness in the regions adjacent to the joints that attach the straight segments to the rest of the ring. This is shown more clearly in FIG. 2.

The incomplete annulus 31 of the angle indicator 30 may optionally have a varying radial thickness around its circumference. Adjacent to the hinges 34 and 35, the radial thickness 36 may be its minimum. The radial thickness may increase farther away from the hinges 34 and 35, reaching an intermediate value 37 partially around the ring, and may finally reach a maximum value 38 directly opposite and between the hinges 34 and 35. Alternatively, the radial thickness may be constant around its circumference, or may vary in a manner other than the exemplary manner described above.

In the exemplary design of FIG. 2, the out-of-plane thickness is essentially constant along the incomplete annulus 31 and segments 32 and 33. The corners may be rounded, or may be un-rounded.

The variation in radial thickness around the ring helps ensure that the incomplete annulus stays essentially round, even as the angle between the straight segments 32 and 33 varies. As such, the diameter dimensions D1, D2 and D3 in FIG. 3 are truly diameters, and the outermost shapes of the angle indicators are essentially round at each of the three sizes shown. The angle indicator 30 retains its round periphery as it is compressed.

Alternatively, the radial thickness of the angle indicator 30 may remain essentially constant around the ring, and the out-of-plane thickness may vary along the ring. As further alternatives, both the radial thickness and the out-of-plane thickness may vary around the ring and/or the radial thickness may remain constant but the material modulus or strength may vary along the ring, for example, being stiffer away from the hinges.

The hinges 34 and 35 may be formed integrally as weakened portions of the angle indicator 30. In one embodiment, the hinges 34 and 35 are formed at regions of reduced in-plane thickness at the intersections of the straight segments 32 and 33 with the incomplete annulus 31. As such, the hinges 34 and 35 may bend freely in the in-plane direction, allowing the angle indicator to freely expand and contract to attain its maximum size inside the capsular bag. The hinges 34 and 35 may be configured to preclude or reduce movement of the two segments 32, 33 out of the plane of the angle indicator 30. Generally, the angle indicator 30 may be made integrally as a single unit, or may be made from several pieces that are assembled. The assembled pieces may be made from the same or from different materials.

The segments 32, 33 are joined to each other by a third hinge 39, formed by an in-plane thickness reduction, also permits free in-plane movement of the segments 32, 33 with respect to each other. The helps to provide free diametric expansion and compression of the angle indicator 30 and restricts out-of-plane movement.

Note that the segments 32 and 33 are shown in the figures as being entirely straight. In practice, there may be some curvature to all or a portion of either or both of the segments. For instance, there may be some local waviness to all or a portion of the segments 32 and 33. Alternatively, there may be a more global curvature, having a radius on the order of or larger than the angle indicator radius. In one embodiment of the angle indicator, the segments 32 and 33 are straight throughout.

Note that the angle indicator 30 may measure capsular bags having a size larger than the incision through which the angle indicator is inserted. For instance, the angle indicator may measure capsular bag diameters on the order of 11 mm. In general, the diameter of the angle indicator in an uncompressed state is at least about 9 millimeters in diameter, but may be between about 8 millimeters and about 15 millimeters, preferably between about 9 millimeters and about 12 millimeters. In some embodiments, the diameter of the angle indicator in an uncompressed state has a nominal value of 11 mm or about 11 mm (i.e., 11 mm plus or minus 0.5 mm). As such, the angle indicator 30 may be compressed in an injector or folded upon itself during insertion (and later, during extraction), and may be unfolded and expanded for performing the measurement. When used in conjunction with an accommodating intraocular lens, the angle indicator is configured to fit through an incision in the eye that is less than about 5 millimeters, preferably less than 4 millimeters. In other embodiments, for example when used with an intraocular lens that does not provide accommodation, the angle indicator is configured to fit through an incision in the eye that is less than about 3 millimeters, preferably less than 2 millimeters.

During insertion and positioning of the angle indicator 30, it may be beneficial to gently "force open" the straight segments 32 and 33 of the angle indicator 30. This may be accomplished by applying a force on or near the rear (essentially flat) side of the hinge 39, directed outward from the ring, toward the opening between the segments. The force may be applied by the practitioner using the equipment that is typically used to position objects during surgery, such as a hook or forceps. Because the force may be applied directly to angle indicator 30, there may be no need for extra holes or tabs for this purpose, although holes and/or tabs may optionally be used.

In certain embodiments, the angle indicator 30 is configured to produce a relatively small force when placed within a capsular bag. For example, the force produced by the angle indicator 30 when the diameter is compressed 2 millimeters may be between about 0.5 gram and about 20 grams, preferably between about 0.5 gram and 5 grams. Such low forces may beneficially reduce the possibility of damaging the capsular bag during use of the angle indicator 30, but may require manipulation by the practitioner to insure that the incomplete annulus 31 fully engages the equatorial region of the capsular bag. Alternatively, a higher force may be used to ensure positive engagement of the equatorial region of the capsular bag with a minimal amount of adjustment by a practitioner, for example, a force of between about 10 grams and about 30 grams or more.

The length of the segments 32 and 33 may be varied, so that the hinge that joins them may fall on either side of the center of the ring at its nominal position. As the segment length is increased, the angle becomes easier for the practitioner to read during use, although the sensitivity is decreased. Likewise, as the segment length is decreased, the angle becomes more difficult for the practitioner to read during use, but the sensitivity is increased. In practice, the designer of ordinary skill in the art understands this trade-off, and may design an angle indicator 30 with a suitable range of operation, a suitable sensitivity, and a suitable ease of angle viewing.

Optionally, there may be more than one angle indicator for a particular eye or patient, with each angle indicator covering a particular range of capsular bag sizes. For instance, one angle indicator may be used for capsular bag diameters in the range of 9 to 10 mm, and another angle indicator may be used for the range 10 to 11 mm. These values are merely exemplary, and any suitable ranges may be used.

Note that because the angle may be measured from roughly the center of the pupil, there is generally little distortion of the angle caused by the cornea. If the cornea imparts a magnification an image of the segments forming the angle, the segments themselves may appear to grow or shrink in size, but the angle between the segments remains essentially unchanged. This holds for a wide range of cornea radii, and a wide range of magnifications caused by the cornea.

It is instructive to perform some trigonometry to more accurately show the graphical dependence of measured angle A and capsular bag diameter D, which is not truly linear as shown schematically in FIG. 3, but has a more complicated dependence.

Figure 4:
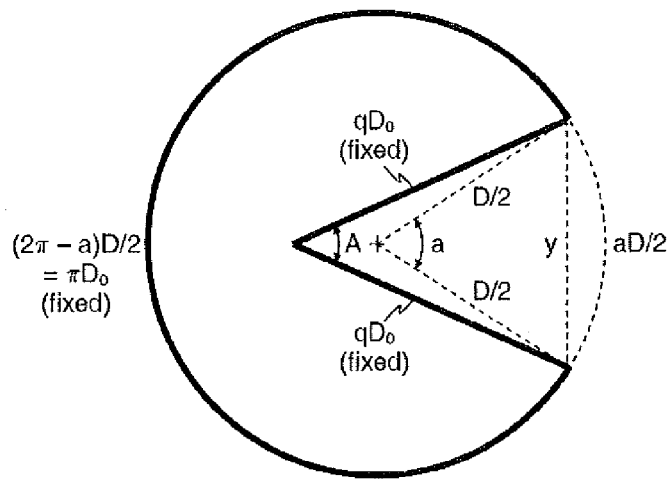
FIG. 4 is a schematic drawing of an approximate geometry of the angle indicator of FIGS. 2 and 3.

FIG. 4 shows an exemplary geometry for one embodiment of an angle indicator. We assume for this simplistic analysis that the lengths of the incomplete annulus (i.e., the open ring-shaped segment) and the straight segments remain constant during use; this is a good approximation for this purpose.

Both the length of the incomplete annulus and the length of each straight segment may be related to a "closed diameter" $D_0$, which is the diameter of the angle indicator when the segments are parallel, or "closed". The length of the incomplete annulus is $\pi D_0$, and the length of each straight segment is $qD_0$, where q is a dimensionless quantity than can between 0 and 1. When q is 0.5, the straight segments extend to exactly the center of the ring when the ring is "closed". When q is 1, the straight segments extend all the way to the opposite end of the ring when the ring is "closed". When q is 0, the straight segments are infinitesimally small.

During use, the angle indicator expands to a diameter of D, with a measured angle A between the straight segments. Length y and angle A are mathematical constructs. We attempt to solve for A in terms of D.

First, solve for y: $y=D \sin(A/2)$.

Next, we express angle A in terms of the length $\pi D_0$ of the incomplete annulus: $A=(2\pi-2\pi D_0/D)$.

Plug into expression for y: $y=D \sin(\pi-\pi D_0/D)=D \sin(\pi D_0/D)$.

Can also solve for y in terms of A and $qD_0$: $y=2 qD_0 \sin(A/2)$

Figure 5:
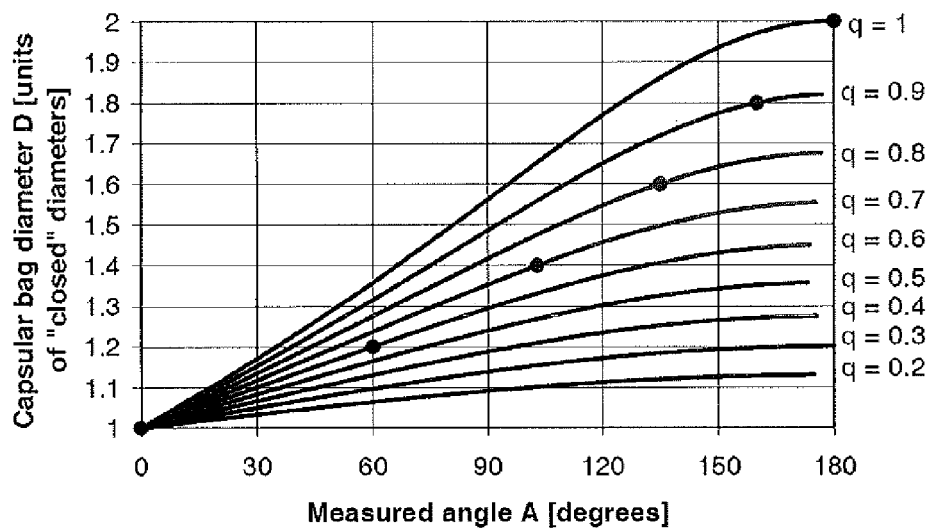
FIG. 5 is a plot of capsular bag diameter versus measured angle A, for a variety of straight segment lengths, for the approximate geometry of FIG. 4.

Set these two expressions for y equal to each other and rearrange to get: $\sin(A/2)=\sin(\pi D_0/D)/(2 qD_0/D)$ Solve for A and rewrite as $A=2 \sin^{-1}([\pi/2q]\times[\sin(\pi D_0/D)/(\pi D_0/D)])$ FIG. 5 is a graph of the above equation, which predicts capsular bag diameter D versus measured angle A, for several values of q.

The choice of q is related to both sensitivity and dynamic range. For relatively short straight segments (low q), there is high sensitivity and low dynamic range. Similarly, for relatively long straight segments (high q), there is low sensitivity and high dynamic range.

In some embodiments, it is preferable if the vertex, or intersection between the straight segments, is located at or near the center of the ring for at least part of the range of use. The circles superimposed on the various plotted curves in FIG. 5 show the operating condition at which the vertex is at the center of the ring. Note that for short segments (q<0.5), there is no condition under which the vertex can be located in the center of the ring; these segments are just too short to extend to the center, regardless of angle A.

Note that for q=0.6 (i.e., where the straight segments are 20% longer than the radius of the "closed" ring), the vertex falls at the center of the ring at a measured angle A of 60 degrees. In one embodiment, this may be a preferable set of conditions; the plotted region for q=0.6 is enlarged and is shown in FIG. 6.

Figure 6:
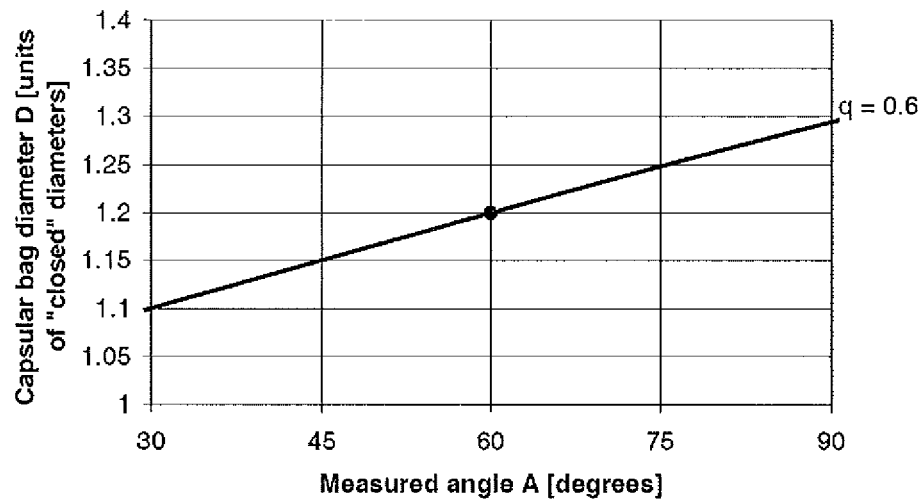
FIG. 6 is a close-up of the q=0.6 plot of FIG. 5.

For FIG. 6, we choose a convenient set of numbers, which are merely exemplary and are not intended to be limiting in any way. For instance, if we wish to measure capsular bags having a diameter in the range of 11 mm to 13 mm, we use an angle indicator having a "closed" diameter of 10 mm and a short segment length of 6 mm, and detect angles between 30 and 90 degrees. If our detection scheme allows us to detect angle A to the nearest 15 degrees, we may measure the diameter of the capsular bag to the nearest 0.5 mm (based on the 10 mm diameter of the angle indicator). These values are merely exemplary, and any lengths and diameters may be scaled upwards or downwards. Other suitable values may also be used.

Note also that the mathematical analysis that generates the plots of FIGS. 5 and 6 is approximate, and assumes that the lengths of the ring-shaped segments and the two straight segments all remain constant throughout operation. This is only an approximation, and one of ordinary skill in the art will readily appreciate that more sophisticated simulations may be performed that account for local stresses and deformations, bending of the materials, and other effects not considered in the simplistic analysis presented above.

The discussion thus far has focused primarily on the angle indicator 30, which generates an angle as a function of the capsular bag size or shape. The following paragraphs focus primarily on measurement devices for estimating or measuring the angle between arms 32, 33 of the angle indicator 30 or other size indicators. For the purposes of this document, the term "measurement device" means any device or system suitable for measuring or estimating a size or location of a size indicator or angle indicator disposed within an eye, for example, by measuring or estimating an angular or linear dimension of one or more elements of the size indicator or angle indicator. The measurement device may, for example, be a sizing gauge, an image processing system, software package, or the like. The measurement device may include software, hardware, firmware, or algorithms suitable for providing a measurement or estimate of a size or location of a size indicator or angle indicator.

For the purposes of this document, the term "sizing gauge" means a physical measurement device suitable for providing an estimate or measurement of a size or location of a size indicator or angle indicator. For example, a sizing gauge may be a template, chart, set of reference images, reticle, protractor, or the like. In certain embodiments, a sizing gauge includes a flexible sheet that may be placed on the eye (e.g., a contact lens) having marks configured for measuring or estimating a dimension of a size indicator or angle indicator. In other embodiments, a sizing gauge may include a calibrated reticle or protractor, which may be used for visual inspection by eye, or used with an optical instrument, such as a microscope or a camera. When used with the angle indicator 30, or similar device, the sizing gauge may include angular increments on the reticle or protractor may include one half degree, one degree, five degrees, 10 degrees, 15 degrees, 20 degrees, 25 degrees, 30 degrees, 35 degrees, 40 degrees, 45 degrees, or any suitable increment. Alternatively, the sizing gauge may be marked with indicia that correspond directly to the capsular bag size or appropriate ranges corresponding to available implant sizes. As used herein, the term "protractor" means a device that can read, measure, or indicate an angle of a size indicator or angle indicator, either by visual inspection or by electronic means.

Figure 7:
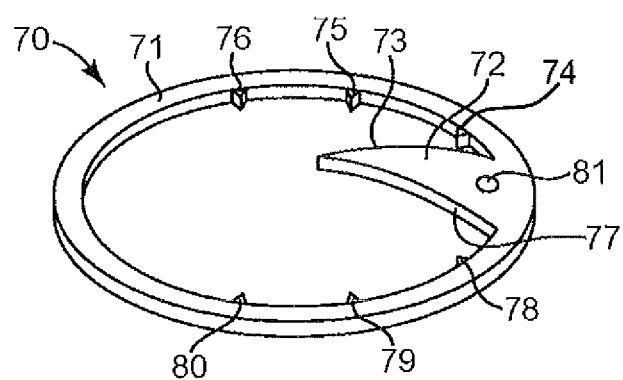
FIG. 7 is an isometric drawing of a protractor according to an embodiment of the present invention.
Figure 8:
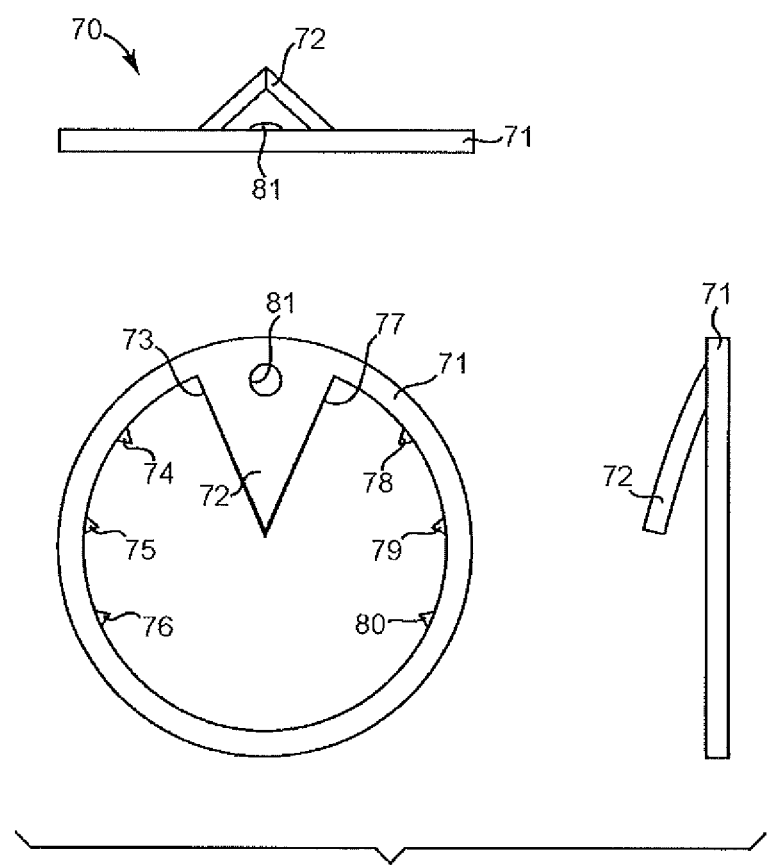
FIG. 8 a set of views of the protractor of FIG. 7.

An exemplary protractor 70 for use with the angle indicator 30, or another size indicator for sizing a capsular bag, is shown in the isometric drawing of FIG. 7 and the three views of the plan drawing of FIG. 8.

The protractor 70 has a generally circular ring 71 that is sized to rest on the cornea to allow measurement of the angle from the angle indicator. The ring 71 is small enough to fit on the eye of the patient, and large enough to surround the pupil of the eye. A typical range of diameters for the protractor ring may be from about 3 mm to about 12 mm, or from about 5 mm to about 8 mm.

Note that the straight segments 32 and 33 of the angle indicator 30 are viewable from roughly the center of the pupil, rather than requiring a measurement taken at the edge of the capsular bag. As a result, ring 71 of the protractor need not extend all the way to the edge of the capsular bag or to the edge of the cornea. The ring 71 may optionally have rounded or chamfered edges that may reduce the risk of scratching the cornea.

The protractor 70 has a reference portion 72 that has radial edges 73 and 77. During use, the reference portion 72 generally extends out of the plane of the ring 71, so that it may rest upon or extend over the cornea, which is curved. When viewed from the front, the intersection of radial edges 73 and 77 may fall at or near the center of the ring 71, and/or at the intersection of the straight segments 32 and 33 (e.g., at the hinge 39). Note that the reference portion 72 may deform so that this intersection of radial edges 73 and 77 may lie away from the center when the protractor is not in use.

In one embodiment, the protractor is rigid, so that the protractor roughly maintains its shape before, during and after use. In this embodiment, the reference portion 72 may extend out of the plane of the ring 71 in its relaxed state before use. Alternatively, the reference portion may 72 may be located roughly in the plane of the ring 71 before use, and may pivot in the anterior direction during use. The pivoting may occur around a weakened portion of the reference portion, which may include an optional hole, opening, or void area 81. In some embodiments, the void area 81 may have a more complex shape that the hole shown in FIG. 7, for example, to provide a weakened zone with predetermined bending characteristics or to avoid confusion that the void area 81 represents an alignment mark with the straight segments 32 and 33.

In another embodiment, the protractor 70 is flexible, and may be draped onto the cornea of the eye. Such a flexible protractor conforms generally to the shape of the cornea, without significantly deforming in the plane of the protractor. The protractor 70 may be made from a largely transparent material, and may include markings or features that indicate predetermined angle values. For instance, the protractor 70 may include a central feature that may be overlaid with the hinge 39 during use, and various angular features, such as reticle marks or other radial lines or features. In one embodiment of a flexible protractor 70, the protractor may be formed on or be made integral with a contact lens that is placed onto the cornea during use.

For the protractor 70 of FIG. 7, the protractor is positioned during use so that one of the radial edges 73 and 77 lines up with one of the straight segments 32 and 33. The other straight segment falls elsewhere around the circumference of the ring, and may fall near one of several calibration features, such as notches, tabs, holes, extensions, annotations, colors or members.

For instance, if radial edge 73 is aligned with straight segment 32, then straight segment 33 may fall near one of feature 74, feature 75 or feature 76. The features may be in calibrated increments, such as 30 degrees, 20 degrees, 15 degrees, 10 degrees, 5 degrees, 1 degree or less, or any suitable increment. For instance, if the increment is 30 degrees between each of the features 74-76, then if the straight segment 32 falls closest to the feature 74, then the angle of the indicator is closest to 30 degrees. Similarly, if the straight segment 32 falls closest to the feature 76, then the angle of the indicator is closest to 90 degrees.

In addition, there is a second set of radial edge 77 and features 78-80, which may be used equally as well as the first set of radial edge 73 and features 74-76. The second set may be calibrated with the same angular increment as the first, or with a different angular increment as the first.

Alternatively, there may be more than three or fewer than three features. In addition, the features may be evenly or unevenly spaced.

Once the measurement has been taken, the protractor 70 may be removed from the cornea of the patient. In one embodiment, the protractor 70 may be removed by grasping it with the hole 81, or by an optional elevated feature or tab (not shown).

In certain embodiments, a more conventional protractor may be used, with notches, tick marks, lines, or other visual cues extending around the circumference at a prescribed interval, such as every 30 degrees, or any other suitable interval. This more conventional protractor may lack the reference portion 72. As another example, the protractor may be made from a soft material that is draped over the cornea or rests on the facial tissue that surrounds the eye, rather than on the eye itself. Alternatively, the angle may be measured from an image formed of the eye on a screen or in software. As a further alternative, there may be an angular reticle supplied with a camera or microscope, which may allow a reading of the angle.

Both the angle indicator 30 and the protractor 70 may be made from any suitable biocompatible and flexible materials. For instance, either or both may be made from silicone or any polymeric material, PMMA, or any other suitable material. In one embodiment, the material or materials used may be moldable, and may not be hydrophilic. In one embodiment, the material is sterilizable by autoclave, by ETO, or by any suitable sterilization process. The angle indicator 30 and protractor 70 may be made from the same or from different materials. Either or both angle indicator 30 and protractor 70 may be made of a transparent or translucent material. Alternatively, either or both angle indicator 30 and protractor 70 may be made of a tinted, opaque or fluorescing material, so that they may easily be read visually. In one embodiment, the angle indicator and protractor may be supplied in pre-sterilized, sealed packages that accompany an intraocular lens. Both the angle indicator and protractor may be unsealed when needed, and disposed of once a measurement has been taken.

In other embodiments, either or both the angle indicator 30 and the protractor 70 may be configured for single-use or a limited number of uses. For example, the protractor 70 may be made of an autoclavable material for reuse in subsequent procedures, while the angle indicator 30 is made of a disposable material that is discarded after one use or after use on a single subject. In such embodiments, the angle indicator 30 or a set of angle indicators 30 may be shipped in a sterile condition along with an intraocular lens to be inserted into a subject eye.

In one embodiment, there may be sets of angle indicators and protractors, with each set corresponding to a different range of capsular bag sizes. For instance, one set may be used for a size range of 9 to 10 mm, and another set may be used for a size range of 10 to 11 mm. Each set may be color-coded so that the particular protractor is easily associated with its corresponding angle indicator, and the measured angles are easily associated with their proper measured capsular bag sizes. Alternatively, there may be other identifying characteristics for matched sets of angle indicators and protractors, such as texture, etching, surface characteristics, ridges and so forth.

In certain embodiments, an electronic or digital image of the angle indicator 30 in the eye and/or the protractor 70 is produced. The digital image may be captured and processed using a computer or other electronic system in order to determine the angle between the two straight sections 32 and 33. The resulting digital representation may be used to increase the accuracy of the angle measurement, as a cross-check to a manual measurement, or to provide other information (e.g., the location of the angle indicator and/or capsular bag within the eye, or to determine a change in size of the capsular bag, as discussed in greater detail below).

In one embodiment, the outer edges of the angle indicator may expand through viscoelastic/OVD in the capsular bag.

In one embodiment, the straight segments, or central arms, of the angle indicator may extend past the center of the angle indicator. These longer straight segments may fill a larger area of the pupil, and may provide an easier measurement than smaller or shorter straight segments.

In one embodiment, the angle indicator may be inserted into the capsular bag by an injector.

In one embodiment, the angle indicator may include a tether, so that the angle indicator may be more easily withdrawn after the measurement has been taken. The withdrawing may be done directly by the tether. Alternatively, the tether may attach the angle indicator to an injector, so that the withdrawal may be done by the injector.

In one embodiment, the angle indicator may include one or more loops on the straight segments or on the incomplete annulus that extend in the anterior direction (i.e., away from the patient's eye), for positioning and removal of the angle indicator.

In one embodiment, the flexural characteristics of the straight segments, or arms, their bases, and/or the central hinge may be "tuned" in shape or stiffness, so that the angle indicator may stay round over a wide range of compression.

In certain embodiments, the angle indicator 30 is made of a silicone material having a hardness of between about 70 durometer and about 80 durometer which approximately corresponds to a modulus of elasticity that may provide a desired compressive force when the angle indicator is placed within a capsular bag. In other embodiments, the modulus of elasticity of the angle indicator material (e.g., silicone or acrylic) and/or the width of the various angle indicator sections may be varied, so that reliable measurements may be made without excessively stretching the capsular bag.

In certain embodiments, the angle indicator 30 may be used to determine or estimate the resiliency of the capsular bag into which it is implanted. For example, the angle indicator 30 may be made of a material having a relatively high modulus of elasticity and/or may be otherwise configured to be relatively resilient or stiff. In some embodiments, two or more angle indicators 30 may be used. For example, a first angle indicator 30' may be inserted into the capsular bag that produces a relatively low force on the capsular bag (e.g., between about 0.1 gram to about 10 grams of force). As such, the first angle indicator 30' may be used to determine the size of the capsular bag when in a substantially unstressed state, as described in greater detail above. The first angle indicator 30' may then be removed from the eye and replaced by a second angle indicator 30" that is stiffer than the first angle indicator 30', thus producing a higher, radially outward force (e.g., in the range of about 5 grams to about 30 grams or more) when compressed by about the same amount as the first angle indicator 30'. Due to the increased force on the capsular bag, the bag is stretched by the second angle indicator 30" and thus produces a different bag size measurement. In some embodiments, the second angle indicator 30" additionally or alternatively has a diameter that is greater than the first angle indicator 30', thereby increasing the force produced on the capsular bag compared to that produced by the first angle indicator 30'. Other differences between the angle indicators 30', 30" may be advantageously used to provide a different radially outward force and/or to determine the resiliency of the capsular bag.

Alternatively, a single angle indicator 30 may be used that remains in the capsular bag; however, the size of the angle indicator 30 and/or on the capsule wall may be changed by increasing or decreasing the radially outward force of the incomplete annulus 31 or exerted on the incomplete annulus 31. The change in force may be produced by changing the resiliency of the angle indicator 30 and/or by inserting another device or apparatus that applies additional force on the equatorial region of the capsular bag and/or angle indicator 30. In some embodiments, a surgeon may change the outward force on the incomplete annulus 31 by using one or more probes or other devices to push or pull at one or more locations on the incomplete annulus 31.

However the difference in size is induced, the resulting size difference may be measured and used to calculate a resiliency of the capsular bag and/or estimate the amount of accommodative force available for accommodation. In some embodiments, the change is size is quantitatively measured to determine a resiliency or other property of the capsular bag. Alternatively, the change in size may be qualitatively assessed so that the surgeon may broadly characterize a resiliency or other property of the capsular bag.

In certain embodiments, the angle indicator 30 is implanted within a capsular bag and the force produced by the ciliary muscle is changed in order to measure a change in the size and/or amount of force produced by the capsular bag. For example, a muscarinic agent such as a muscarinic agonist or a muscarinic antagonist may be used to alter the amount of accommodative force produced by the eye, as disclosed in U.S. Pat. No. 6,598,606 or US Patent Application Number 2005/0251254, which are herein incorporated by reference.

In one embodiment, a plurality of angle indicators 30 is provided in the form of a kit, with each angle indicator 30 having a different elasticity or tensile strength. Such a kit may be used to determine the elasticity of a particular evacuated capsular bag, in order to best determine the most compatible accommodating intraocular lens.

In one embodiment, the angle indicators 30 are provided in a kit, with each angle indicator 30 having a different axial thickness. Such a kit may help match the measurement of the capsular bag size to the axial thickness of the intended implanted intraocular lens, both at the edge of the lens and centrally.

In one embodiment, the arms 32, 33 include overlapping, curved vernier extensions. With reference to the exemplary design of FIG. 2, arm 32 may include one or more tangentially-curved extensions that protrude toward arm 33, and arm 33 may also include one or more tangentially-curved extensions that protrude toward arm 32, with the tangentially-curved extensions being located next to each other. In this manner, the angle may be read directly from the extensions, rather than with an additional external device such as a measurement device or sizing gauge.

In one embodiment, the incomplete annulus 31 may include extensions or tabs protruding from one or both of the straight segments 32, 33 and disposed along the circumference of, and in the plane of, the incomplete annulus 31. These optional extensions may help maintain the capsular circularity in the region between the straight segments 32, 33.

In addition to measuring the capsular bag size for intraocular lens implantation, the angle indicator 30, or variations thereof, may be used for other fields as well, such as measuring the diameters and stenosis of body cavities, especially in endoscopic and catheter-based procedures for sizing shunts and implants. The angle indicator allows estimation of a particular diameter, regardless of viewing magnification. This may also be used in the fields of interventional cardiology, as well as vascular, bariatric and gastroenteric surgeries. Furthermore, the angle indicator 30, or variations thereof, may also be used to measure the size of the anterior chamber or other cavities of the eye.

Referring to FIGS. 9-11, in some embodiments, a sizing gauge 102 is configured for measuring or estimating a size of a size indicator (e.g., the angle indicator 30) or for measuring or estimating a size or other characteristic of a capsular bag or other cavity into which a size indicator is inserted. Where applicable, the sizing gauge 102 incorporate features and functions of the protractor 70 discussed above, or visa versa.

In the illustrated embodiments in FIG. 11, the sizing gauge 102 is part of a measurement system comprising an angle indicator 90 and the sizing gauge 102, the system configured for measuring a size or other characteristic of a capsular bag of an eye. The angle indicator 90 may be similar or equal to the angle indicator 30. The angle indicator 90 includes a peripheral portion 92 configured to contact a capsular bag of a subject eye and a pair of arms 94 operably coupled to the peripheral portion 92 and joined at an intersection of the arms 94. The arms 94 are configured so that an angle formed by the arms 94 varies in response to a size of the capsular bag and/or other property, such as a resiliency or elasticity of the capsular bag.

The sizing gauge 102 comprises a body 110 having a front surface 112. Various features of sizing gauge 102 are visible when viewed from in front of the front surface 112, these features being useful for measuring an angle of the angle indicator 90 or similar device. Any or all of these features may be disposed on the front surface 112 and/or on a surface of the sizing gauge 102 that is opposite the front surface 112. Alternatively, at least some of the features may be disposed between front and back surfaces of the sizing gauge 102, for example, on a laminate surface that is between front and back surfaces of the sizing gauge 102.

In the illustrated embodiment, the sizing gauge 102 includes an inner portion 115, an outer portion 118, and a border or boundary 120 disposed therebetween. The boundary 120 is configured to provide a comparison, estimate, or measurement of an angle of the arms 92 of the angle indicator 90 when the sizing gauge 102 is disposed in front of the angle indicator 90.

Optionally, the sizing gauge 102 may comprise a handle or grip 128, as illustrated in FIG. 10 for the sizing gauge 102'. The handle 128 may be sized and configured to allow the sizing gauge 102' to be held by a practitioner in order to move the sizing gauge 102' into a desired location and orientation in front of the angle indicator 90. Additionally or alternatively, the handle 128 may be configured to be held by a robotic or automated positioning device that is controlled either by an electronic controller configured to move the sizing gauge 102 relative to the angle indicator 90.

The sizing gauge 102, 102' may be made of a metal or polymer material, or any material suitable for a clinical environment and providing necessary physical properties. The sizing gauge 102, 102' may be made of a single material or may comprises different materials. For example, the handle 128 of the sizing gauge 102' may be made of a different material than the rest of the sizing gauge 102'. In some embodiments, all or portions of the sizing gauge may be made of a transparent or substantially transparent material, for example, in order to facilitate viewing of the angle indicator 90 when used therewith.

The inner portion 115 may be an opening or aperture 124 in the body 110, wherein the boundary 120 is an inside edge of sizing gauge 102. In such embodiments, the outer portion 118 may be made of either a transparent material or an opaque material. The aperture 124 and the boundary 120 are configured to allow the angle between the pair of arms 94 of the angle indicator 90 to be estimated or measured.

In some embodiments, the inner and outer portions 115, 118 are made of a common or similar material, wherein the boundary 120 is a border between the portions 115, 118. In such embodiments, the inner and outer portions 115, 118 may both be made of a transparent, semi-transparent, or clear material, wherein the border 120 may be dark, opaque, or otherwise configured to allow delineation between the inner and outer portions 115, 118. Alternatively, at least one of the portions 115, 118 may be opaque, colored, translucent, frosted, darkened, or only partially transparent, while the other portion 118, 115 may transparent or semitransparent.

The border 120 in the illustrated embodiments comprises a quadrilateral shape 125 in which opposite vertices 126a, 126b join sides of the quadrilateral to form angles that are different from one another, the angles being selected to correspond different angles between the pair of arms of the angle indicator 90. The sizing gauge 102, 102' may further comprise alphanumeric characters 130, for example, in the inner or outer portions 115, 118 and/or indicating a size or other value correlating to one or more angles of the angle indicator 90.

During use one of the vertices 126a, 126b is aligned to a vertex of the angle indicator 90 located at the intersection of the arms 94. As illustrated in FIG. 11, the angle between the sides forming the vertex 126b is approximately equal to the angle formed by the arms 94 of the angle indicator 90. The alphanumeric "10 mm" near the vertex 126b indicates that the match or approximate match between these two angles correlates to a capsular bag diameter of 10 mm or approximately 10 mm. Alternatively, the alphanumeric characters on the sizing gauge 102 may be used to indicate or correlate to other quantities such as, an angle between the pair of arms of the angle indicator 90, a circumference, cross-sectional area, or volume of the capsular bag, a resiliency of the capsular bag, or the like.

The outer portion 118, inner portion 115, surface 112, and/or the back surface opposite surface 112 of sizing gauge 102, 102' may be either planar or curved. If curved, the radius of curvature may be selected to allow the sizing gauge to be draped over the cornea of an eye. For example, the sizing gauge 102 may be a contact lens that has a radius of curvature that is approximately equal to the radius of curvature of the cornea. Alternatively, the surface curvature of the sizing gauge 102' may be configured to fit or closely fit the shape of the cornea. In any event, the sizing gauge 102, 102' may be configured to have little or no optical power. Alternatively, the sizing gauge 102, 102' may be configured to have an optical power, for example, a negative optical power that at least partially compensates or nullifies the optical power of the cornea of an eye. In other embodiments, the optical power is selected to provide a desired magnification or to form part of an imaging system configured to view the angle indicator 90 or a portion of the eye into which the angle indicator 90 is implanted.

In some embodiments, a kit comprising a plurality of sizing gauges 102 is provided, for example, with each sizing gauge 102 have a different radius of curvature or shape. Additionally or alternatively, the kit may include a plurality of sizing gauges 102, wherein different sizing gauges 102 have different included angle between the sides of the inner portion 115.

Referring to FIGS. 12 and 13, in some embodiments, a sizing gauge 202 is configured for measuring or estimating a size of a size indicator (e.g., angle indicators 30, 90) or for measuring or estimating a size or other characteristic of a capsular bag or other cavity into which a size indicator is inserted. Where applicable, the sizing gauge 202 incorporate features and functions of the protractor 70 and/or the sizing gauges 102, 102' discussed above, or visa versa. In the illustrated embodiments in FIG. 13, the sizing gauge 202 is part of a measurement system comprising the angle indicator 90 and the sizing gauge 202, the system being configured for measuring a size or other characteristic of a capsular bag of an eye.

The sizing gauge 202 comprises a body 210 having a front surface 212 and various features that are visible when viewed from in front of the front surface 212, these features being useful for measuring an angle of the angle indicator 90 or similar size indicator. Like the sizing gauge 102, the features of the sizing gauge 202 may be disposed on one or more of the front or back surfaces of the sizing gauge 202, or between the front and back surfaces.

The sizing gauge 202 comprises a first feature 224 and a second feature 226 that are disposed on or behind the surface 212. The first feature 224 is a vertex mark 224 that is configured to be aligned to the vertex of the angle indicator 90 formed at the intersection of the arms 94. In the illustrated embodiment, the vertex mark 224 comprises an aperture that may be a through hole in the body 210 or may comprise a clear material, for example, the same material as the remaining portions of the body 210. Alternatively, the vertex mark 94 comprises a pair of crosshairs, a bull's eye pattern, or other marking suitable for facilitating alignment of the sizing gauge 202 to the intersection of the arms 94 of angle indicator 90.

The second feature 226 of the sizing gauge 202 comprises three lines that are disposed parallel to one another and perpendicular to a longitudinal axis of the sizing gauge 202. In other embodiments, the second feature comprises a different number of lines (e.g., 2 lines or 4 lines). In any event, the lines 226 are disposed a different distances from the vertex mark 224 and may have different lengths, as in the illustrated embodiment shown in FIG. 12. The endpoints of each line 226 and the center of vertex mark 224 are configured to correspond to different angles between the arms 94 of the angle indicator 90.

Referring to FIG. 13, during use, the vertex mark 224 of the sizing gauge 202 is aligned to an intersection between arms 94 of the angle indicator 90. The angle of between the arms 94 may be determined or estimated based upon which of the line 226 endpoints touches, or is closest to touching, a predetermined part of the arms 94 (e.g., an inner or outer edge of each of the arms 94). In this manner, the measured or estimated angle between the arms 94 may be correlated to a size or other property of the capsular bag into which the angle indicator 90 has been placed. In the illustrated embodiment, alpha numeric characters 230 are disposed near the lines 226 to show a correspondence of the lines 226 to a capsular bag size of either 9.5 mm, 10 mm, or 10.5 mm. It is not necessary that each line be associated with a particular alphanumeric character 230. For example, in FIGS. 13 and 14 the sizing gauge 202 does not have an alphanumeric symbol associated with the center line 226, but it is understood that if the arms of the angle indicator just touch the center line 226, then this correlates to a capsular bag diameter of 10 mm.

Referring to FIG. 14, in some embodiments, a sizing gauge 302 is configured for measuring or estimating a size of a size indicator (e.g., angle indicators 30, 90) or for measuring or estimating a size or other characteristic of a capsular bag or other cavity into which a size indicator is inserted. Where applicable, the sizing gauge 302 incorporate features and functions of the protractor 70 and/or the sizing gauges 102, 102', 202 discussed above, or visa versa. In the illustrated embodiments in FIG. 14, the sizing gauge 202 may be part of a measurement system that comprises the angle indicator 90 and the sizing gauge 302, the system being configured for measuring a size or other characteristic of a capsular bag.

The sizing gauge 302 comprises a body 310 having a front surface 312 and various features that are visible when viewed from in front of the front surface 312, these features being useful for measuring an angle of the angle indicator 90 or other size indicator. Like the sizing gauges 102, 102', 202, the various features of the sizing gauge 302 may be disposed on one or more of front or back surfaces of the sizing gauge 202, or between the front and back surfaces. The body 310 of the sizing gauge 302 may be made of a clear, colored, frosted, or opaque material, according to the requirements of the user or manufacturer.

The body 310 comprises a pair of notches or wedge-shaped features 324 disposed along side and top edges of the body 310. The use of two wedge-shaped features 324 may be configured to allow easy manipulation of the sizing gauge 302 in order to align one of the wedge-shaped feature 324 to the arms 94. In the illustrated embodiment, each wedge-shaped feature 324 has the same angular extent—in this case both angles corresponding to a capsular bag size of 10.8 mm. Alternatively, each of the wedge-shaped features 324 may have a different angle between the edges of the wedge-shaped feature, for example, to facilitate measurement of different arm 94 angles with a single sizing gauge 302. In some embodiments, the sizing gauge 302 comprises only one wedge-shaped feature 324. In other embodiments, the sizing gauge 302 comprises three wedge-shaped features 324 or more than three wedge-shaped features 324.

The sizing gauge 302 in the illustrated embodiment comprises an elongated body 312; however, other shapes may be used. For example, two, three, four, or more wedge-shaped features 324 may be configured on a circular body, wherein each of the wedge-shaped features 324 has a different angle between the edges of the wedge-shaped features 324.

Figure 15:
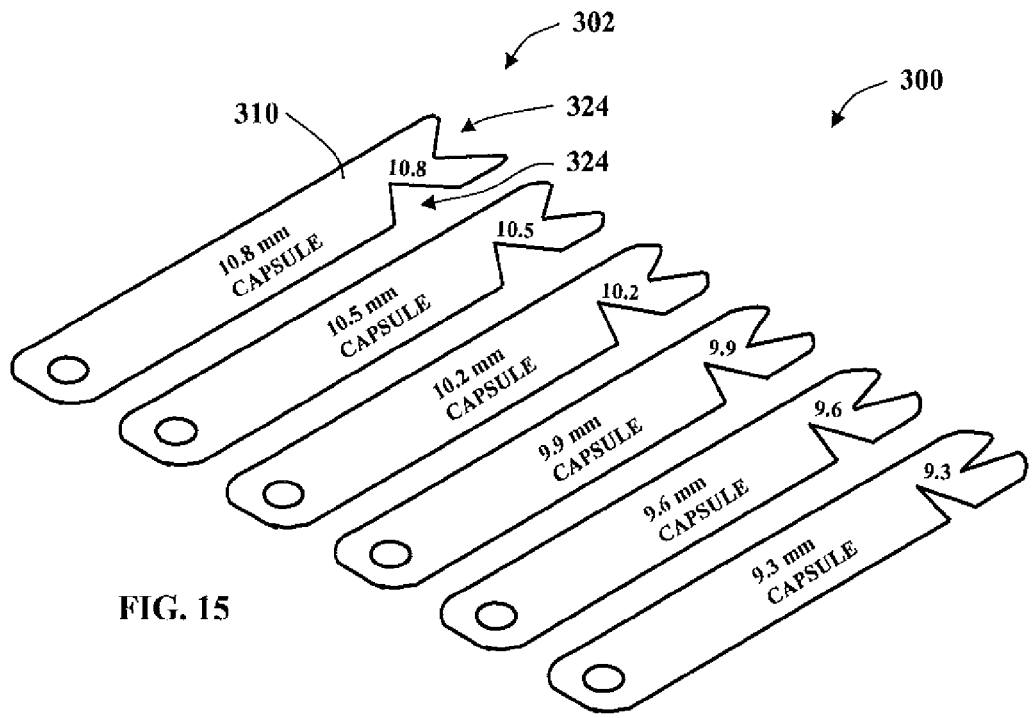
FIG. 15 is a perspective view of a kit or set of sizing gauges like the sizing gauge shown in FIG. 14.
Figure 16:
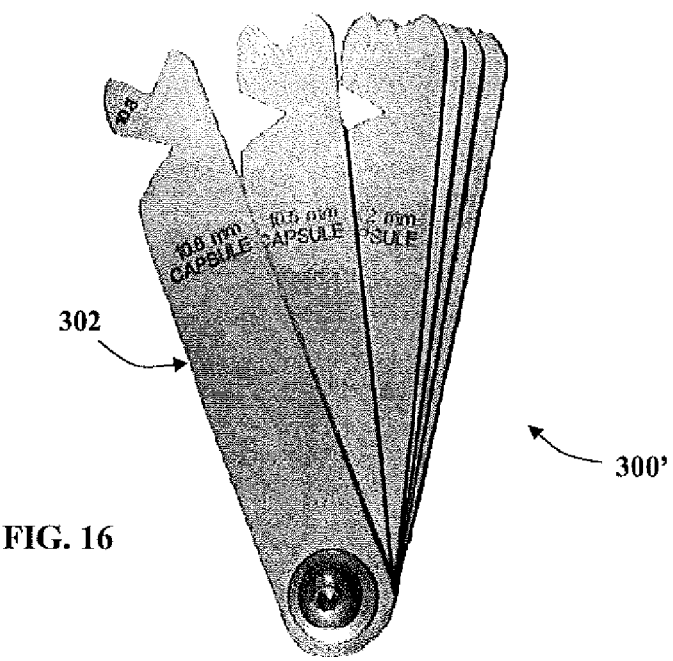
FIG. 16 is a front view of a kit or set of sizing gauges like the sizing gauge shown in FIG. 14 that are joined together to facilitate choosing different gauges during use.

Referring to FIGS. 15 and 16, the sizing gauge 302 may be part of a kit or set 300 or 300' of sizing gauges 302 that are used for estimating or measuring the size or other property of a capsular bag. The sizing gauges 302 in the set 300' are attached together at a proximal end of each sizing gauge 302, for example, to facilitate easy selection between individual gauges 302 during use.

During use, the angle indicator 90 is disposed within the capsular bag of an eye or inside another portion or cavity of the eye. One of the sizing gauges 302 of the kit 300 or 300' is then selected and located in front of the angle indicator 90 or other size indicator. The sizing gauge is next aligned to the angle indicator 90 so that a vertex 330 (see FIG. 14) of the wedge-shaped features 324 is disposed at the intersection of the pair of arms 94 of the angle indicator 90, and so that at least one of the edges of the wedge-shaped feature 324 is aligned to at least one edge of one of the arms 94. An assessment can then be made as to whether or not the angle of the wedge-shaped feature is sufficiently close to the angle between the arms 94. If so, then the angle may be correlated to a size of the angle indicator or a size or other property of the capsular bag into which the angle indicator 90 has been placed. If the angles do not match, then another sizing gauge 302 from the kit 300, 300' is selected and the process is repeated until a correspondence is found between the angle of the wedge-shaped feature 324 and the angle between the arms 94 of the angle indicator 90.

The description of the invention and its applications as set forth herein is illustrative and is not intended to limit the scope of the invention. Variations and modifications of the embodiments disclosed herein are possible, and practical alternatives to and equivalents of the various elements of the embodiments would be understood to those of ordinary skill in the art upon study of this patent document. These and other variations and modifications of the embodiments disclosed herein may be made without departing from the scope and spirit of the invention.

What is claimed is:

1. A system for measuring the size of a capsular bag of an eye, comprising:
   a size indicator configured for insertion into a capsular bag of a subject eye and comprising a peripheral portion and a pair of arms, the peripheral portion configured to engage the capsular bag, the pair of arms each having proximal and distal ends, the arms joined to one another at the proximal ends, the peripheral portion joined to the distal ends of the arms, the arms forming an angle that depends on a size of the capsular bag, the angle being within a predetermined range of angles when the size indicator is placed within the capsular bag; and
   a sizing gauge for measuring or estimating a size of the size indicator.

2. The system of claim 1, wherein the arms of the size indicator are configured so that an angle formed by the arms varies in response to a dimension of the capsular bag.

3. The system of claim 1, wherein the size of the capsular bag is a diameter of the capsular bag.

4. The system of claim 1, wherein the size of the capsular bag is a volume of the capsular bag.

5. The system of claim 1, wherein the sizing gauge comprises a protractor that can read, measure or indicate an angle of the size indicator by visual inspection or electronically.

* * * * *